(12) United States Patent
Cheng et al.

(10) Patent No.: US 8,445,120 B2
(45) Date of Patent: May 21, 2013

(54) TRIPHENYLENE BASED AROMATIC COMPOUNDS AND OLEDS UTILIZING THE SAME

(75) Inventors: Chien-Hong Cheng, Hsinchu (TW); Fang-Iy Wu, Hsinchu (TW); Yin-Yen Tsai, Hsinchu (TW); Yu-Han Chen, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 13/517,607

(22) Filed: Jun. 14, 2012

(65) Prior Publication Data

US 2012/0248429 A1   Oct. 4, 2012

Related U.S. Application Data

(62) Division of application No. 12/762,364, filed on Apr. 18, 2010.

(51) Int. Cl.
*H01L 51/54* (2006.01)

(52) U.S. Cl.
USPC ........... 428/690; 428/917; 313/504; 313/505; 313/506; 257/40; 257/E51.05; 257/E51.026; 257/E51.032; 548/440

(58) Field of Classification Search
USPC ..... 428/690, 917; 313/504, 505, 506; 257/40, 257/E51.05, E51.026, E51.032; 585/27; 548/440
See application file for complete search history.

(56) References Cited

U.S. PATENT DOCUMENTS

| 2006/0088728 A1* | 4/2006 | Kwong et al. ................ 428/690 |
| 2006/0280965 A1 | 12/2006 | Kwong et al. |
| 2009/0169921 A1 | 7/2009 | Cheng et al. |
| 2010/0295030 A1* | 11/2010 | Kawamura ...................... 257/40 |

OTHER PUBLICATIONS

Pope et al., "Electroluminescence in Organic Crystals", Journal of Chemical Physics, 38(8), 2042-2043, 1963.
Tang et al., "Organic electroluminescent diodes", Appl. Phys. Lett., 51(12), 913-915, Sep. 21, 1987.
Burroughes et al., "Light-emitting diodes based on conjugated polymers", Nature, vol. 347, 539-541, Oct. 11, 1990.

* cited by examiner

*Primary Examiner* — Jennifer Chriss
*Assistant Examiner* — Gregory Clark
(74) *Attorney, Agent, or Firm* — Pai Patent & Trademark Law Firm; Chao-Chang David Pai

(57) ABSTRACT

Disclosed is a triphenylene based aromatic compound, wherein a benzene center is substituted with a triphenylene group and another aromatic group such as triphenylenyl, pyrenyl, phenylvinyl, carbazolylphenyl, or arylanthryl in the meta position of the benzene center. The meta-substituted aromatic compound of the invention has better thermal stability (Tg) than the conventional para-substituted aromatic compound. The meta-substituted aromatic compound, served as a hole transporting layer or a host material applied in a light emitting layer in an OLED, is more preferable than the conventional para-substituted aromatic compound.

5 Claims, No Drawings

TRIPHENYLENE BASED AROMATIC COMPOUNDS AND OLEDS UTILIZING THE SAME

CROSS REFERENCE TO RELATED APPLICATIONS

This application is a Divisional of pending U.S. patent application Ser. No. 12/762,364, filed on Apr. 18, 2010 and entitled "Triphenylene based aromatic compounds and OLEDs utilizing the same", which claims priority of Taiwan Patent Application No. 099103141, filed on Mar. 8, 2010, the entirety of which is incorporated by reference herein.

BACKGROUND OF THE INVENTION

1. Field of the Invention

The present invention relates to a triphenylene based aromatic compound, and in particular relates to an organic light emitting diode utilizing the same.

2. Description of the Related Art

The earliest report of organic electroluminescence was made by Pope et al in 1963, who observed a blue fluorescence from 10-20 μm of crystalline anthracene by applying voltage across opposite sides of the crystal. Thus, starting a wave of first improvements in organic electroluminescence research. However, difficulties of growing large areas of crystals were a challenge. The driving voltage of the device was too high and the efficiency of organic materials was lower than inorganic material. Because of the disadvantages of the devices, the devices were not widely applied due to practical purposes.

However, a major development in organic electroluminescence technology was reported in 1987. Tang and VanSlyke of Eastman Kodak Company used vacuum vapor deposition and novel hetero junction techniques to prepare a multilayered device with hole/electron transporting layers. 4,4-(cyclohexane-1,1-diyl)bis(N,N-dip-tolylbenzenamine) (TPAC) was used as a hole transporting layer, and $Alq_3$ (tris(8-hydroxyquinolinato)aluminum(III)) film with good film-forming properties was used as an electron transporting and emitting layer. A 60-70 nm-thick film was deposited by vacuum vapor deposition with a low-work function Mg:Ag alloy as a cathode for efficient electron and hole injections. The bi-organic-layer structure allowed the holes and electrons to recombine at the p-n interface and then emit light. The device emitted green light of 520 nm, and was characterized by low driving voltage (<10 V), high quantum efficiency (>1%) and good stability. The improvements, once again, arouse interest in organic electroluminescence research.

Meanwhile, Calvendisg and Burroughes et al. at Cambridge University in 1990 was the first to report using conjugated polymer PPV (poly(phenylene vinylene)) as an emitting layer in a single-layered device structure by solution spin coating. The development of an emitting layer with conjugated polymer drew great interest and quickly sparked research due to the simplicity of fabrication, good mechanical properties of polymer, and semiconductor-like properties. In addition, a large number of organic polymers are known to have high fluorescence efficiencies.

In U.S. patent application Ser. No. 11/968,353, the inventor of the invention had disclosed the triphenylene derivatives application in blue light emitting device. In previously application, the aromatic center had two substituents such as triphenylenyl group, pyrenyl group, or combinations thereof. When the aromatic center was benzene, the two substituents were para-substituted on the benzene. This application only focused on tuning the center aromatic types, however, it did not disclose the different substituted positions of the substituents and the influences thereof.

Accordingly, methods and corresponding formulae are called for to reduce the symmetry of the triphenylene based aromatic compound. In addition, the methods without largely changing the synthetic steps and the corresponding formulae may enhance the thermal stability (such as Tg) and luminescence property (such as external quantum efficiency) of the device utilizing the triphenylene based aromatic compound.

BRIEF SUMMARY OF THE INVENTION

The invention provides a triphenylene based aromatic compound, having a general formula:

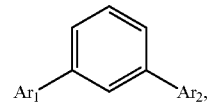

wherein $Ar_1$ is a triphenylenyl group; $Ar_2$ is a triphenylenyl group, a pyrenyl group, a phenylvinyl group, a carbazolylphenyl group, or an arylanthryl group.

The invention also provides an organic light emitting diode, comprising: an anode; a cathode; and an organic layer disposed between the anode and the cathode, wherein the organic layer comprises the described triphenylene based aromatic compound.

A detailed description is given in the following embodiments.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The invention provides triphenylene based aromatic compounds serving as a hole transporting layer or a host material in a light emitting layer of OLEDs. Because the triphenylene based aromatic compounds have excellent thermal stability and luminescence efficiency, they may further enhance the brightness, the external quantum efficiency, the current efficiency, and the power efficiency of a device utilizing the same.

The triphenylene based aromatic compounds are synthesized as below. When both of the two meta-substituted groups of the compound are the triphenylenyl groups, the compound can be synthesized as shown in Formula 1:

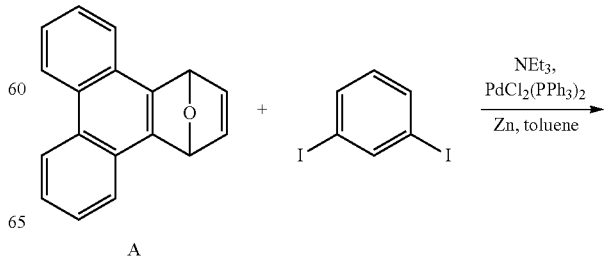

(Formula 1)

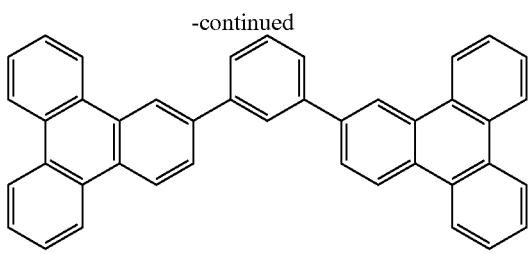

The synthesis of the starting material A in Formula 1 is disclosed in U.S. patent application Ser. No. 11/968,353 and thus is omitted here.

When the two meta-substituted groups of the compound are a triphenylenyl group and another aromatic group, respectively, the compound can be synthesized by Formula 2, followed by Formula 3 (Suzuki coupling).

(Formula 2)

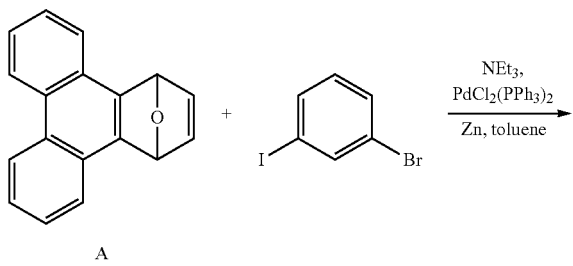

(Formula 3)

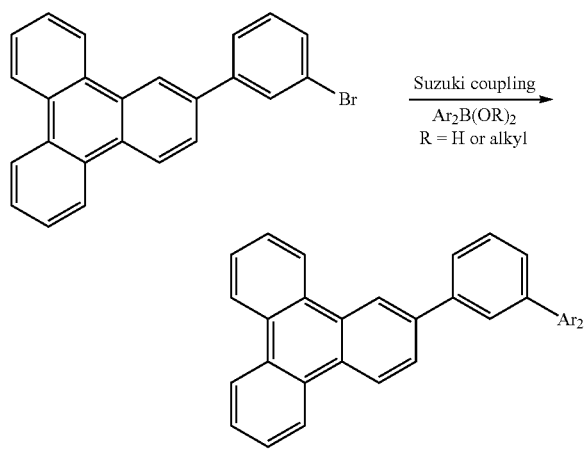

The $Ar_e$ in Formula 3 is an aromatic group such as a triphenylenyl group, pyrenyl group, a phenylvinyl group, a carbazolylphenyl group, or an arylanthryl group. In one embodiment, the arylanthryl group includes pyridinylanthryl group, a phenylanthryl group, a naphthenylanthryl group, a biphenylanthryl group, or a carbazolylanthryl group The boron-containing starting material is prepared by following steps. n-BuLi is added to an aromatic bromide for metal-halogen exchange. The boron agent and the HCl/pinacol are sequentially added to the resulting of the metal-halogen exchange, thereby forming boric acid or boric ester.

In one embodiment, the triphenylenyl group, $Ar_2$, and a benzene center of the triphenylene based aromatic compound independently have one or more substituents selected from the group consisting of hydrogen, halogen, aryl, halogen-substituted aryl, halogen-substituted aryl alkyl, haloalkyl-substituted aryl, haloalkyl-substituted aryl alkyl, aryl-substituted $C_{1-20}$ alkyl, electron donating group, electron withdrawing group, and heterocyclic-substituents. The electron donating group includes a $C_{1-20}$ alkyl group, a $C_{1-20}$ alkoxyl group, a $C_{1-20}$ alkyl amino group, or an aryl amino group. The electron withdrawing group includes a nitrile group, a nitro group, a carbonyl group, a cyano group, or a halogenated $C_{1-20}$ alkyl group.

The invention further provides an organic light emitting diode (OLED), including an anode, a cathode, and a light emitting layer disposed between the anode and the cathode, wherein the light emitting layer includes the described triphenylene based aromatic compound. The anode includes indium tin oxide, indium zinc oxide, aluminum zinc oxide, or combinations thereof. The anode can be formed by evaporation or sputtering. The cathode includes inorganic conductive material such as magnesium silver alloy, calcium, lithium fluoride, aluminum, or combinations thereof. The cathode can be formed by evaporation or sputtering. In one embodiment, a hole injecting layer, a hole transporting layer, and/or other suitable layered materials can be disposed between the light emitting layer and the anode. The hole injecting layer includes molybdenum trioxide, copper phthalocyanine, poly (3,4-ethylenedioxythiophene):poly(styrenesulfonate) (PEDOT:PSS), N,N'-di-phenyl-N,N'-di-[4-(N,N-di-phenyl-amino)phenyl]benzidine (NPNPB) and 4,4',4"-tris(N-3-methylphenyl-N-phenyl-amino)-triphenylamine (m-TDATA). The hole transporting layer includes 4'4',4"-tris (carbazol-9-yl)-triphenylamine (TCTA), N,N'-diphenyl-N, N'-bis(3-methylphenyl)-1,1'-biphenyl)-4,4'-diamine (TPD), or N,N'-bis(1-naphyl)-N,N'-diphenyl-1,1'-biphenyl-4,4'-di-amine (NPB).

In one embodiment, an electron injecting layer, an electron transporting layer, an electron blocking layer, and/or other suitable layered materials can be disposed between the light emitting layer and the cathode. The electron injecting layer includes alkali halide, alkaline-earth halide, alkali oxide, or alkali carbonate, such as LiF, CsF, NaF, $CaF_2$, $Li_2O$, $Cs_2O$, $Na_2O$, $Li_2CO_3$, $Cs_2CO_3$, or $Na_2CO_3$. The electron transporting layer includes tris(8-hydroxy quinoline) aluminum (Alq3) or 2,2',2"-(1,3,5-benzinetriyl)-tris(1-phenyl-1-H-benzimidazole) (TPBI). The hole blocking layer includes 2,9-dimethyl-4,7-diphenyl-1,10-phenanthroline (BCP), aluminum (III) bis(2-methyl-8-quninolinato)-4-phenylphenolate (BAlq), bis(10-hydroxybenzo[h]qinolinato)beryllium (BeBq2) or 2,2',2"-(1,3,5-Benzinetriyl)-tris(1-phenyl-1-H-benzimidazole) (TPBI).

The light emitting layer may be further doped with other dopants such as BCzVBi as shown in Formula 4. As such, the luminescence efficiency of the OLED is enhanced by the host-guest system.

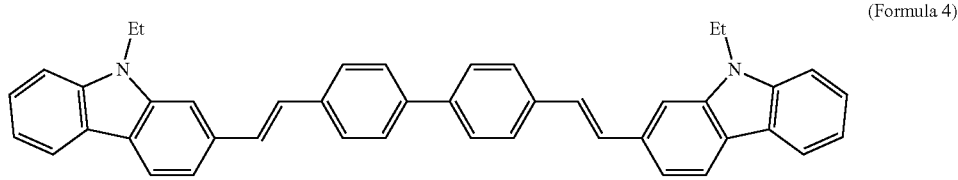 [SMILES: CCn1c2ccccc2c2ccc(/C=C/c3ccc(-c4ccc(/C=C/c5ccc6c7ccccc7n(CC)c6c5)cc4)cc3)cc21]

(Formula 4)

In another embodiment, other conventional host materials and dopants are selected as be the light emitting layer of the OLED, and the described triphenylene based aromatic compounds may serve as the hole transporting layer of the OLED. Because the triphenylene based aromatic compounds of the invention have low HOMO value, thereby efficiently transporting the hole. In addition, the material and the formation of the other layered structures such as the cathode, the electron injecting layer, the electron transporting layer, the hole blocking layer, the hole injecting layer, and the anode can be similar to that which was previously described.

EXAMPLES

Example 1

As shown in Formula 1, the compound A (1.00 g, 4.1 mmol), 1,3-diiodobenzene (0.63 g, 1.9 mmol), zinc (2.69 g, 41.4 mmol), and $PdCl_2(PPh_3)_2$ (0.44 g, 0.6 mmol) were charged in a two-necked bottle. The bottle was then vacuumed and purged with nitrogen, and dried toluene (88 mL) and triethyl amine (5.75 mL, 41.5 mmol) were added to the bottle. The mixture in the bottle was heated to 100° C. for reaction for 24 hours, and the resulting was filtered to remove metal. The filtrate was condensed to remove the solvent, and then purified by chromatography with an eluent of dichloromethane/n-hexane (1:6) to obtain a product. The product was sublimated at a temperature of 305° C. to obtain a white solid of 0.57 g (yield=56%).

The white solid product in Formula 1 was dissolved in dichloromethane to form a solution having a concentration of $10^{-5}$M, or evaporated to form a film having a thickness of 30 nm. The absorption-emission peaks of the film and the solution are tabulated in Table 1.

The spectra data of the product in Formula 1 is shown as follows. $^1$H NMR (400 MHz, $CDCl_3$): δ 9.02 (s, 2H), 8.85-8.81 (m, 4H), 8.75-8.70 (m, 6H), 8.30 (s, 1H), 8.08 (dd, J=8.6, 1.6 Hz, 2H), 7.92 (dd, J=8.6, 1.6 Hz, 2H), 7.75-7.71 (m, 9H). $^{13}$C NMR (125 MHz, $CDCl_3$): δ 142.8, 140.9, 131.2, 131.1, 130.9, 130.6, 130.2, 130.1, 128.2, 128.1, 128.1, 127.4, 127.3, 124.9, 124.5, 124.3, 124.3, 122.7. HRMS (m/z): [M$^+$] calculated for $C_{42}H_{26}$:530.2035; found: 530.2034. Element Analysis: calculated for $C_{42}H_{26}$: C, 95.06; H, 4.94. found: C, 94.82; H, 4.90.

Example 2

As shown in Formula 2, compound A (4.00 g, 16.4 mmol), zinc (10.72 g, 163.9 mmol), and $PdCl_2(PPh_3)_2$ (1.16 g, 1.7 mmol) were charged in a two-necked bottle. The bottle was then vacuumed and purged with nitrogen, and dried toluene (350 mL), 1-bromo-3-iodobenzene (2.08 mL, 16.4 mmol), and triethyl amine (5.75 mL, 41.5 mmol) were added to the bottle. The mixture in the bottle was heated to 100° C. for reaction for 24 hours, and the resulting was filtered to remove metal. The filtrate was condensed to remove the solvent, and then purified by chromatography with an eluent of n-hexane to obtain a white solid of 3.42 g (yield=54%). The white solid product in Formula 2 was dissolved in dichloromethane to form a solution having a concentration of $10^{-5}$M, or evaporated to form a film having a thickness of 50 nm. The absorption-emission peaks of the film and the solution are tabulated in Table 1.

The spectra data of the product in Formula 2 is shown as follows. $^1$H NMR (400 MHz, $CDCl_3$): δ 8.79 (s, 1H), 8.74-8.64 (m, 5H), 7.93 (s, 1H), 7.83 (d, J=8.4 Hz, 1H), 7.72-7.66 (m, 5H), 7.53 (d, J=7.6 Hz, 1H), 7.38 (t, J=7.6 Hz, 1H). $^{13}$C NMR (125 MHz, $CDCl_3$): δ 143.2, 138.2, 130.4, 130.3, 130.0, 130.0, 129.8, 129.5, 129.4, 129.3, 128.3, 127.4, 127.4, 127.3, 127.3, 126.0, 126.0, 124.0, 123.3, 123.3, 123.3, 123.0, 121.7. HRMS (m/z): [M$^+$] calculated for $C_{24}H_{15}Br$, 382.0357; found, 382.0352.

As shown in Formula 3, the product in Formula 2 (1.00 g, 2.6 mmol), pyren-1-ylboronic acid (0.64 g, 2.6 mmol, synthesized by Example 2 in U.S. patent application Ser. No. 11/968,353), potassium carbonate solution (2.0 M, 6.50 mL), and dried toluene (27 mL) were charged in a two-necked bottle. The bottle was deoxygenated and purged with nitrogen, and the mixture in the bottle was stirred at 60° C. until it was totally dissolved. The nitrogen pressure of the bottle was increased, and $Pd(PPh_3)_4$ (0.15 g, 0.1 mmol) was rapidly added into the bottle. The reaction was heated to 100° C., and stirred for 48 hours. The resulting was cooled to room temperature to precipitate a solid, and the solid was collected by filtering. The solid was washed by water and toluene, and then sublimated at a temperature of 280° C. to obtain a yellow solid of 0.69 g (yield=52%) as shown in Formula 5.

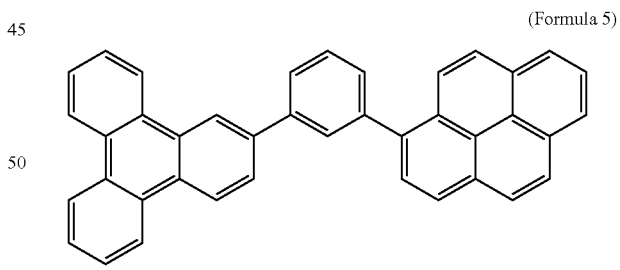

(Formula 5)

The yellow solid compound in Formula 5 was dissolved in dichloromethane to form a solution having a concentration of $10^{-5}$ M, or evaporated to form a film having a thickness of 30 nm. The absorption-emission peaks of the film and the solution are tabulated in Table 1.

The spectra data of the compound in Formula 5 is shown as follows. $^1$H NMR (400 MHz, $CDCl_3$): δ 9.01 (s, 1H), 8.79-8.70 (m, 5H), 8.33 (d, J=8.8 Hz, 2H), 8.27-8.17 (m, 2H), 8.16-8.05 (m, 7H), 8.00 (d, J=7.2 Hz, 1H), 7.79-7.68 (m, 6H). $^{13}$C NMR (125 MHz, $CDCl_3$): δ 141.9, 141.2, 139.6, 137.6, 131.5, 131.0, 130.7, 130.2, 130.0, 129.8, 129.7, 129.6, 129.1, 129.0, 128.6, 127.7, 127.6, 127.5, 127.4, 127.4, 127.3, 127.3, 127.3, 126.4, 126.3, 126.1, 125.3, 125.2, 125.0, 124.9, 124.7, 124.0, 123.4, 123.3, 121.9. HRMS (m/z): [M⁺] calculated for $C_{40}H_{24}$, 504.1878; found, 504.1881. Element Analysis: calculated for $C_{40}H_{24}$: C, 95.21; H, 4.79. found: C, 95.12; H, 4.78.

Example 3

(2-bromoethene-1,1,2-triyl)tribenzene (5.00 g, 14.9 mmol) was charged in a reaction bottle. The reaction bottle was then heated, vacuumed, and purged with nitrogen. Dried tetrahydrofuran (50 mL) was added to the reaction bottle and stirred until (2-bromoethene-1,1,2-triyl)tribenzene was dissolved, and the solution was cooled to −78° C. n-BuLi (15.00 mL, 30.00 mmol, 2.0 M n-hexane solution) was dropwise added to the cooled solution, and the reaction was stirred at −78° C. for 1 hour. Subsequently, B(OBu)₃ (11.00 mL, 40.8 mmol) was added to the reaction for reaction for another 8 hours. The resulting mixture was acidified by HCl (2.0 M, 300 mL) for 3 hours. The acidified mixture was extracted by ethyl acetate to collect the organic layer thereof. The organic layer was dried by MgSO₄ and then condensed to precipitate a solid. The solid was washed by n-hexane and filtered to obtain a white solid of 2.91 g (yield=65%) as shown in Formula 6.

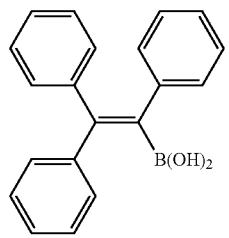

(Formula 6)

The spectra data of the compound in Formula 6 is shown as follows. ¹H NMR (400 MHz, CDCl₃): δ 7.37-7.30 (m, 5H), 7.17-7.02 (m, 8H), 6.91-6.88 (m, 2H), 4.08 (s, 2H). ¹³C NMR (100 MHz, CDCl₃): δ 153.2, 143.7, 142.3, 142.0, 130.7, 129.8, 129.3, 128.6, 128.4, 128.2, 127.6, 127.0, 126.2. HRMS (m/z): [M⁺] calculated for $C_{20}H_{17}BO_2$, 300.1322; found, 300.1323.

The product in Formula 2 (1.00 g, 2.6 mmol), the compound in Formula 6 (0.78 g, 2.6 mmol), potassium carbonate solution (2.0 M, 6.50 mL), and dried toluene (27 mL) were charged in a two-necked bottle. The two-necked bottle was deoxygenated and purged with nitrogen, and the mixture in the bottle was stirred at 60° C. until it was totally dissolved. The nitrogen pressure of the bottle was increased, and Pd(PPh₃)₄ (0.15 g, 0.1 mmol) was rapidly added into the bottle. The reaction was heated to 100° C., and stirred for 48 hours. The resulting was filtered to remove metal, and then condensed to remove the solvent to obtain a solid. The solid was washed by ethyl ether, filtered, and then sublimated at a temperature of 290° C. to obtain a pale yellow solid of 0.72 g (yield=50%) as shown in Formula 7.

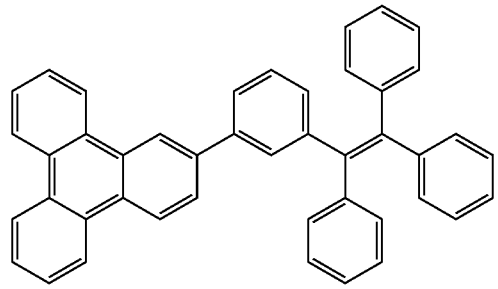

(Formula 7)

The compound in Formula 7 was dissolved in dichloromethane to form a solution having a concentration of 10⁻⁵ M, or evaporated to form a film having a thickness of 30 nm. The absorption-emission peaks of the film and the solution are tabulated in Table 1.

The spectra data of the compound in Formula 7 is shown as follows. ¹H NMR (400 MHz, CDCl₃): δ 8.65-8.54 (m, 5H), 8.32 (s, 1H), 7.68-7.63 (m, 4H), 7.57-7.50 (m, 3H), 7.32-7.26 (m, 3H), 7.23-7.04 (m, 14H). ¹³C NMR (125 MHz, CDCl₃): δ 144.1, 144.0, 143.7, 143.6, 141.3, 140.9, 140.2, 139.8, 131.6, 131.4, 131.3, 131.0, 130.4, 129.9, 129.9, 129.7, 129.7, 129.6, 128.7, 128.3, 127.9, 127.7, 127.7, 127.2, 127.2, 127.1, 126.9, 126.7, 126.5, 126.5, 126.3, 125.5, 123.6, 123.6, 123.3, 121.6. HRMS (m/z): [M⁺] calculated for $C_{44}H_{30}$, 558.2348; found, 558.2349. Elemental Analysis: calculated for $C_{44}H_{30}$: C, 94.59; H, 5.41. found: C, 94.60; H, 5.42.

Example 4

(2-bromoethene-1,1-diyl)dibenzene (2.00 g, 7.7 mmol) was charged in a reaction bottle. The reaction bottle was then heated, vacuumed, and purged with nitrogen. Dried tetrahydrofuran (30 mL) was added to the reaction bottle and stirred until (2-bromoethene-1,1-diyl)dibenzene was dissolved, and the solution was cooled to −78° C. n-BuLi (4.64 mL, 11.6 mmol, 2.5 M n-hexane solution) was dropwise added to the cooled solution, and the reaction was stirred at −78° C. for 1 hour. Subsequently, B(OBu)₃ (1.32 mL, 11.6 mmol) was added to the reaction for reaction for another 8 hours. The resulting mixture was acidified by HCl (2.0 M, 300 mL) for 3 hours. The acidified mixture was extracted by ethyl acetate to collect the organic layer thereof. The organic layer was dried by MgSO₄ and then condensed to precipitate a solid. The solid was washed by n-hexane and filtered to obtain a white solid of 1.21 g (yield=70%) as shown in Formula 8.

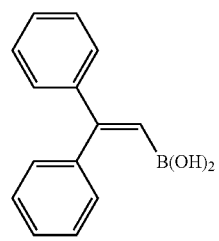

(Formula 8)

The product in Formula 2 (200 mg, 0.52 mmol), the compound in Formula 8 (128.6 mg, 0.57 mmol), potassium carbonate solution (2.0 M, 6.50 mL), and dried toluene (27 mL) were charged in a two-necked bottle. The two-necked bottle was deoxygenated and purged with nitrogen, and the mixture in the bottle was stirred at 60° C. until it was totally dissolved. The nitrogen pressure of the bottle was increased, and Pd(PPh₃)₄ (57.8 mg, 0.05 mmol) was rapidly added into the bottle. The reaction was heated to 100° C., and stirred for 48 hours. The resulting was filtered to remove metal, and then condensed to remove the solvent to obtain a solid. The solid was washed by ethyl ether, filtered, and then sublimated at a temperature of 250° C. to obtain a white solid of 139 mg (yield=55%) as shown in Formula 9.

(Formula 9)

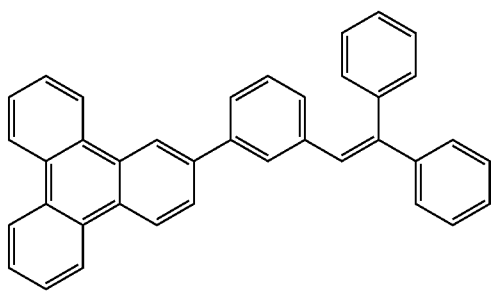

The spectra data of the compound in Formula 9 is shown as follows. $^1$H NMR (400 MHz, CDCl₃): δ 8.66-8.58 (m, 5H), 8.46 (d, J=1.6 Hz, 1H), 7.71-7.61 (m, 5H), 7.55 (d, J=7.6, 1H), 7.47-7.43 (m, 4H), 7.39-7.31 (m, 8H), 7.16 (d, J=7.6, 1H), 7.09 (s, 1H).

Example 5

9H-carbazole (1.67 g, 10.0 mmol), 1-bromo-4-iodobenzene (3.39 g, 12.0 mmol), copper (I) iodide (0.19 g, 1.0 mmol), L-proline (0.23 g, 2.0 mmol), and potassium carbonate (2.76 g, 20.0 mmol) were charged in a two-necked bottle. The bottle was then vacuumed and purged with nitrogen. Dimethyl sulfoxide (25 mL) was added to the bottle. The mixture in the bottle was heated to 90° C. and stirred for 48 hours. The resulting was extracted by dichloromethane and water. The organic layer of the extraction was dried by MgSO₄, condensed, and purified by chromatography with an eluent of n-hexane to obtain a white solid of 2.09 g (yield=65%) as shown in Formula 10.

(Formula 10)

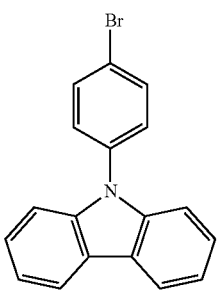

The spectra data of the compound in Formula 10 is shown as follows. $^1$H NMR (400 MHz, CDCl₃): δ 8.12 (d, J=8.0 Hz, 2H), 7.71 (d, J=8.4 Hz, 2H), 7.44 (d, J=8.4 Hz, 2H), 7.40 (t, J=7.6 Hz, 2H), 7.35 (d, J=8.0 Hz, 2H), 7.28 (t, J=7.2 Hz, 2H). $^{13}$C NMR (100 MHz, CDCl₃): δ 140.6, 136.8, 133.1, 128.7, 126.0, 123.5, 120.8, 120.4, 120.2, 109.5. HRMS (m/z): [M⁺] calculated for C₁₈H₁₂BrN, 321.0153; found, 321.0145.

The compound in Formula 10 (1.60 g, 5.0 mmol) was charged in a reaction bottle. The reaction bottle was then heated, vacuumed, and purged with nitrogen. Dried tetrahydrofuran (80 mL) was added to the reaction bottle and stirred until the compound in Formula 10 was totally dissolved, and the solution was cooled to −78° C. n-BuLi (2.40 mL, 6.0 mmol, 2.5 M n-hexane solution) was dropwise added to the cooled solution, and the reaction was stirred at −78° C. for 1 hour. Subsequently, B(OCH₃)₃ (0.86 mL, 7.5 mmol) was added to the reaction for reaction for another 8 hours. The resulting was extracted by ethyl ether and water. The organic layer of the extraction was dried by MgSO₄, and condensed to obtain a solid.

The solid was charged in a reaction bottle. Benzene (15 mL) and pinacol (1.20 g, 10.2 mmol) were added to the reaction bottle. The mixture was heated to 120° C. to reflux for 2 hours. The resulting was directly condensed, and recrystallized by n-hexane and chloroform to obtain a white solid of 1.04 g (yield=57%) as shown in Formula 11.

(Formula 11)

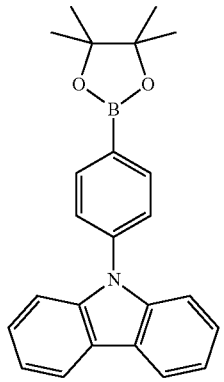

The spectra data of the compound in Formula 11 is shown as follows. $^1$H NMR (400 MHz, CDCl₃): δ 8.12 (d, J=7.6 Hz, 2H), 8.03 (d, J=8.4 Hz, 2H), 7.58 (d, J=8.0 Hz, 2H), 7.42 (t, J=8.0 Hz, 2H), 7.38 (d, J=7.6 Hz, 2H), 7.27 (t, J=7.6 Hz, 2H), 1.38 (s, 12H). $^{13}$C NMR (100 MHz, CDCl₃): δ 140.6, 140.3, 136.4, 126.1, 125.9, 125.5, 120.3, 120.0, 109.8, 109.7, 84.1, 24.9. HRMS (m/z): [M⁺] calculated for C₂₄H₂₄BNO₂, 369.1900; found, 369.1897.

The product in Formula 2 (1.04 g, 2.7 mmol), the compound in Formula 11 (1.00 g, 2.7 mmol), potassium carbonate solution (2.0 M, 6.70 mL), and dried toluene (28 mL) were charged in a two-necked bottle. The two-necked bottle was deoxygenated and purged with nitrogen, and the mixture in the bottle was stirred at 60° C. until it was totally dissolved. The nitrogen pressure of the bottle was increased, and Pd(PPh₃)₄ (0.16 g, 0.1 mmol) was rapidly added into the bottle. The reaction was heated to 100° C., and stirred for 48 hours. The resulting was filtered to remove metal, and then condensed to remove the solvent to obtain a solid. The solid was washed by ethyl ether, filtered, and then sublimated at a temperature of 290° C. to obtain a white solid of 0.94 g (yield=63%) as shown in Formula 12.

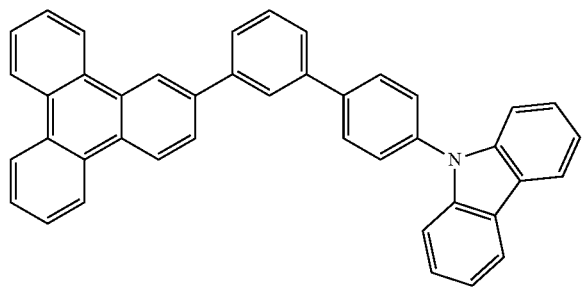

(Formula 12)

The compound in Formula 12 was dissolved in dichloromethane to form a solution having a concentration of $10^{-5}$ M, or evaporated to form a film having a thickness of 30 nm. The absorption-emission peaks of the film and the solution are tabulated in Table 1.

The spectra data of the compound in Formula 12 is shown as follows. $^1$H NMR (400 MHz, CDCl$_3$): δ 8.93 (s, 1H), 8.79-8.66 (m, 5H), 8.16 (d, J=7.6 Hz, 2H), 8.10 (s, 1H), 7.98 (d, J=8.4 Hz, 1H), 7.93 (d, J=8.0 Hz, 2H), 7.84 (d, J=7.6 Hz, 1H), 7.75-7.64 (m, 8H), 7.51 (d, J=8.0 Hz, 2H), 7.43 (t, J=8.0 Hz, 2H), 7.30 (t, J=7.6 Hz, 2H). $^{13}$C NMR (125 MHz, CDCl$_3$): δ 141.9, 141.0, 140.8, 140.1, 139.6, 137.0, 130.1, 130.0, 129.8, 129.7, 129.5, 129.1, 128.6, 127.4, 127.3, 127.3, 127.2, 126.7, 126.3, 126.3, 126.3, 126.0, 123.9, 123.4, 123.4, 123.3, 123.3, 121.8, 120.3, 120.0, 109.8. HRMS (m/z): [M$^+$] calculated for C$_{42}$H$_{27}$N, 545.2143; found, 545.2153. Elementary Analysis calculated for C$_{42}$H$_{27}$N: C, 92.45; H, 4.99; N, 2.57. found: C, 92.39; H, 5.03; N, 2.56.

Example 6

9,10-dibromoanthracene (4.00 g, 11.9 mmol), phenylboronic acid (1.60 g, 13.1 mmol), potassium carbonate solution (2.0 M, 24.00 mL), and dried toluene (70 mL) were charged in a two-necked bottle. The two-necked bottle was deoxygenated and purged with nitrogen, and the mixture in the bottle was stirred at 60° C. until it was totally dissolved. The nitrogen pressure of the bottle was increased, and Pd(PPh$_3$)$_4$ (0.68 g, 0.6 mmol) was rapidly added into the bottle. The reaction was heated to 100° C., and stirred for 48 hours. The resulting was filtered to remove metal. The filtrate was extracted by the dichloromethane. The organic layer of the extraction was dried by MgSO$_4$, condensed, and purified by chromatography with an eluent of n-hexane to obtain a yellow solid of 2.08 g (yield=52%) as shown in Formula 13.

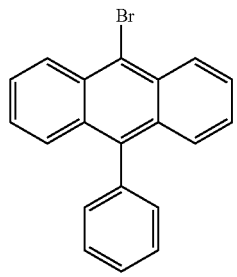

(Formula 13)

The spectra data of the compound in Formula 13 is shown as follows. $^1$H NMR (400 MHz, CDCl$_3$): δ 8.61 (d, J=8.8 Hz, 2H), 7.65 (d, J=8.8 Hz, 2H), 7.63-7.55 (m, 5H), 7.42-7.38 (m, 4H). $^{13}$C NMR (100 MHz, CDCl$_3$): δ 138.4, 137.8, 131.1, 131.0, 130.2, 128.4, 127.8, 127.7, 127.4, 126.9, 125.5, 122.7. HRMS (m/z): [M$^+$] calculated for C$_{20}$H$_{13}$Br, 332.0201; found, 332.0202.

The compound in Formula 13 (1.50 g, 4.5 mmol) was charged in a reaction bottle. The reaction bottle was then heated, vacuumed, and purged with nitrogen. Dried tetrahydrofuran (24 mL) was added to the reaction bottle and stirred until the compound in Formula 13 was dissolved, and the solution was cooled to −78° C. n-BuLi (2.16 mL, 5.4 mmol, 2.5 M n-hexane solution) was dropwise added to the cooled solution, and the reaction was stirred at −78° C. for 1 hour. Subsequently, B(OCH$_3$)$_3$ (0.78 mL, 6.8 mmol) was added to the reaction for reaction for another 8 hours. The resulting was extracted by ethyl ether and water. The organic layer of the extraction was dried by MgSO$_4$, and condensed to obtain a solid.

The solid was charged in a reaction bottle. Benzene (15 mL) and pinacol (1.07 g, 9.1 mmol) were added to the reaction bottle. The mixture was heated to 120° C. to reflux for 2 hours. The resulting was directly condensed, and purified by chromatography with an eluent of ethyl acetate/n-hexane (1:40) to obtain a yellow solid of 1.00 g (yield=58%) as shown in Formula 14.

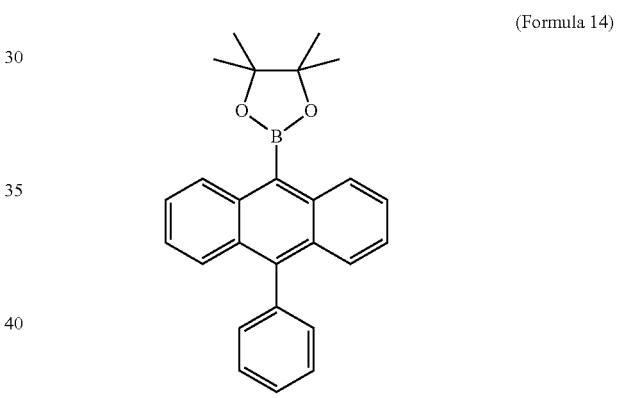

(Formula 14)

The spectra data of the compound in Formula 14 is shown as follows. $^1$H NMR (400 MHz, CDCl$_3$): δ 8.42 (d, J=8.8 Hz, 2H), 7.61 (d, J=8.8 Hz, 2H), 7.57-7.48 (m, 3H), 7.45 (t, J=7.6 Hz, 2H), 7.37 (d, J=6.4 Hz, 2H), 7.29 (t, J=7.6 Hz, 2H), 1.59 (s, 12H). $^{13}$C NMR (100 MHz, CDCl$_3$): δ 139.5, 139.1, 135.3, 131.0, 129.7, 128.3, 128.3, 127.4, 125.4, 124.8, 84.5, 25.2. HRMS (m/z): [M$^+$] calculated for C$_{26}$H$_{25}$BO$_2$, 380.1948; found, 380.1956.

The product in Formula 2 (1.21 g, 3.2 mmol), the compound in Formula 14 (1.20 g, 3.2 mmol), potassium carbonate solution (2.0 M, 7.8 mL), and dried toluene (33 mL) were charged in a two-necked bottle. The two-necked bottle was deoxygenated and purged with nitrogen, and the mixture in the bottle was stirred at 60° C. until it was totally dissolved. The nitrogen pressure of the bottle was increased, and Pd(PPh$_3$)$_4$ (0.18 g, 0.2 mmol) was rapidly added into the bottle. The reaction was heated to 100° C., and stirred for 48 hours. The resulting was cooled to precipitate a solid. The solid was collected by filtering, washed by water and methanol, and sublimated at 260° C. to obtain a yellow solid of 0.97 g (yield=55%) as shown in Formula 15.

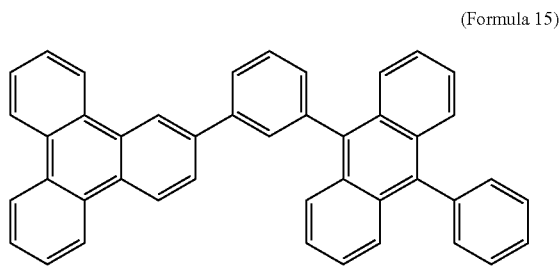 [SMILES: c1ccc(-c2c3ccccc3c(-c3cccc(-c4ccc5c6ccccc6c6ccccc6c5c4)c3)c3ccccc23)cc1]

(Formula 15)

The compound in Formula 15 was dissolved in dichloromethane to form a solution having a concentration of $10^{-5}$ M, or evaporated to form a film having a thickness of 50 nm. The absorption-emission peaks of the film and the solution are tabulated in Table 1.

The spectra data of the compound in Formula 15 is shown as follows. $^1$H NMR (400 MHz, CDCl$_3$): δ 8.95 (s, 1H), 8.72-8.64 (m, 5H), 8.03-7.97 (m, 3H), 7.84 (dd, J=7.2, 2.0 Hz, 2H), 7.77 (t, J=8.0 Hz, 1H), 7.72 (dd, J=7.2, 2.0 Hz, 2H), 7.67-7.49 (m, 10H), 7.39-7.33 (m, 4H). $^{13}$C NMR (125 MHz, CDCl$_3$): δ 141.1, 140.2, 140.1, 139.8, 139.3, 139.0, 137.3, 136.9, 131.3, 130.6, 130.1, 130.0, 129.9, 129.8, 129.7, 129.5, 129.1, 129.0, 128.4, 127.8, 127.5, 127.4, 127.3, 127.2, 127.0, 127.0, 126.4, 126.3, 126.1, 125.2, 125.1, 124.0, 123.6, 123.4, 123.3, 121.8. HRMS (m/z): [M$^+$] calculated for C$_{44}$H$_{28}$, 556.2191; found, 556.2196. Elementary Analysis: calculated for C$_{44}$H$_{28}$: C, 94.93; H, 5.07. found: C, 94.71; H, 5.12.

TABLE 1

| | Solution type | | Film type | |
|---|---|---|---|---|
| | Absorption peaks (nm, molar extinction coefficient ($10^4$ M$^{-1}$ cm$^{-1}$)) | Emission peak (nm) | Absorption peak (nm) | Emission peak (nm) |
| Product in Formula 1 | 232 (12.17), 270 (12.96), 310 (5.37) | 368 | 280, 324 | 408 |
| Formula 5 | 274 (11.80), 315 (35.60), 332 (38.50), 345 (45.40) | 383, 400 | 277, 353 | 464 |
| Formula 7 | 274 (14.06), 304 (6.72) | 383, 401 | 271, 321 | 467 |
| Formula 9 | 271 (8.72), 304 (4.96) | 379 | Not measured | Not measured |
| Formula 12 | 266 (23.07), 293 (12.78), 305 (9.95) | 375, 394 | 261, 296, 319 | 388 |
| Formula 15 | 261 (221.8), 306 (3.33), 357 (1.36), 375 (2.10), 395 (1.97) | 412, 431 | 369, 361, 381, 403 | 429, 444 |

As tabulated in Table 2, the solutions of the white solid product in Formula 1, the yellow solid compound in Formula 5, the pale yellow solid compound in Formula 7, the white solid compound in Formula 9, the white solid compound in Formula 12, and the yellow solid compound in Formula 15 were measured by cyclic voltammetry, respectively, to obtain their HOMO, LUMO, and energy gap between the HOMO and LUMO.

TABLE 2

| | Product in Formula 1 | Formula 5 | Formula 7 | Formula 9 | Formula 12 | Formula 15 |
|---|---|---|---|---|---|---|
| HOMO (eV) | 5.90 | 5.66 | 5.74 | 5.90 | 5.66 | 5.56 |
| LUMO (eV) | 2.09 | 2.32 | 2.28 | 2.18 | 2.09 | 2.41 |
| Energy gap (eV) | 3.81 | 3.34 | 3.46 | 3.72 | 3.57 | 3.15 |

Table 2 indicates that the triphenylene based aromatic compounds in the invention have lower HOMO, thereby benefiting the hole transporting. As such, the light emitting layer utilizing the triphenylene based aromatic compounds in the invention may eliminate the so-called hole transporting layer. Meanwhile, the triphenylene based aromatic compounds in the invention may serve as the hole transporting layer integrated with other conventional light emitting layers to further improve device performance.

Example 7

The glass transition temperature (Tg), the crystal temperature (Tc), and the melting temperature (Tm) of the product in Formula 1, the compound in Formula 5, the compound in Formula 7, the compound in Formula 12, the compound in Formula 15, and the compound in Formula 16 (synthesized in J. Phys. Chem. C 113, 7405 (2009)) were analyzed by a DSC with a rising temperature rate of 10° C./minute under nitrogen, respectively. The thermal analysis data of those compounds are tabulated in Table 3.

TABLE 3

(Formula 16)

| | Tg (° C.) | Tc (° C.) | Tm (° C.) |
|---|---|---|---|
| Product in Formula 1 | 127 | 210 | 275 |
| Formula 5 | 116 | None | None |
| Formula 7 | 108 | None | 220 |
| Formula 12 | 118 | None | 223 |
| Formula 15 | 135 | None | 285 |
| Formula 16 | None | None | 393 |

As shown in Table 3, although both of the product in Formula 1 and the compound in Formula 16 have a benzene center and two triphenylenyl substituents, the meta-substituted product in Formula 1 has better thermal stability than the para-substituted compound in Formula 16. The compound in Formula 16 does not have Tg. Thus, it is easily crystallized by heating. In addition, the compound in Formula 16 has higher Tm. Thus, increasing process difficulty due to be easily solidified on the wall of the evaporation boat while being evaporated. Accordingly, the meta-substituted compound in the invention has better thermal stability than the conventional para-substituted compound.

Example 8

In one example, the ITO was served as an anode, 50 nm of TCTA served as a hole transporting layer, 30 nm of the host material (such as the product in Formula 1, the compound in Formula 5, the compound in Formula 7, the compound in Formula 12, and the compound in Formula 15) served as a light emitting layer, 10 nm of the BCP served as a hole blocking layer, 30 nm of $Alq_3$ served as a electron transporting layer, 1 nm of LiF served as a electron injecting layer, and 100 nm of Al served as a cathode were sequentially formed on the ITO anode. In another example, the ITO was served as an anode, 50 nm of NPB served as a hole transporting layer, 30 nm of the host material (such as the compound in Formula 16) served as a light emitting layer, 10 nm of the BCP served as a hole blocking layer, 30 nm of $Alq_a$ served as a electron transporting layer, 55 nm of magnesium silver alloy served as a electron injecting layer, and 100 nm of Ag served as a cathode were sequentially formed on the ITO anode. The external quantum efficiency (E.Q.E.), the current efficiency (C. E.), the power efficiency (P. E.), the maximum brightness, the driving voltage, and the CIE coordination of the devices are tabulated in Table 4.

TABLE 4

| Light emitting layer | E.Q.E. (%) (V) | C.E. (cd/A) | P.E. (lm/W) | Max brightness (cd/m²) (V) | Driving voltage (V) | CIE coordination |
|---|---|---|---|---|---|---|
| Formula 16 | 2.5 (8.0) | 3.39 | 1.41 | 15285 (20.5) | 4.0 | (0.15, 0.16) |
| Product in Formula 1 | 2.65 (8.5) | 0.89 | 0.34 | 1939 (15.0) | 5.8 | (0.16, 0.66) |
| Formula 5 | 4.35 (9.5) | 4.54 | 1.80 | 22100 (19.0) | 4.7 | (0.15, 0.12) |
| Formula 7 | 2.49 (9.0) | 4.31 | 1.58 | 10310 (15.5) | 6.2 | (0.17, 0.24)) |
| Formula 12 | 0.93 (7.5) | 0.51 | 0.22 | 1627 (16.0) | 6.0 | (0.16, 0.09) |
| Formula 15 | 3.96 (8.0) | 2.41 | 1.07 | 6011 (13.5) | 4.6 | (0.15, 0.07) |

As shown in Table 4, the best device luminescence performance is achieved by the light emitting layer adopting the compound in Formula 5.

Example 9

Example 9 was similar to Example 8, except that the light emitting layer in Example 9 was further doped with 3% of BCzVBi. The external quantum efficiency (E.Q.E.), the current efficiency (C. E.), the power efficiency (P. E.), the maximum brightness, the driving voltage, and the CIE coordination of the devices are tabulated in Table 5.

TABLE 5

| Host material in the Light emitting layer | E.Q.E. (%) (V) | C.E. (cd/A) | P.E. (lm/W) | Max brightness (cd/m²) (V) | Driving voltage (V) | CIE coordination |
|---|---|---|---|---|---|---|
| Formula 16 | 4.93 (6.0) | 6.22 | 3.74 | 17797 (17.0) | 4.2 | (0.15, 0.16) |
| Product in Formula 1 | 6.06 (4.5) | 8.4 | 5.88 | 33800 (16.0) | 4.5 | (0.14, 0.18) |
| Formula 5 | 9.17 (9.5) | 12.99 | 6.23 | 63362 (20.0) | 4.2 | (0.14, 0.19) |
| Formula 7 | 8.33 (7.0) | 8.94 | 4.73 | 23600 (18.0) | 5.2 | (0.14, 0.12) |
| Formula 12 | 5.35 (7.5) | 6.28 | 2.80 | 25012 (17.5) | 4.4 | (0.14, 0.14) |
| Formula 15 | 7.58 (8.5) | 9.41 | 3.61 | 36244 (16.5) | 5.5 | (0.15, 0.15) |

As shown in Table 5, the dopant BCzVBi may further improve device luminescence performance. In addition, the meta-substituted compound is more preferable to be the host material in the light emitting layer than the conventional para-substituted compound. For further reference, see comparison of the compound in Formula 16 and the product in Formula 1.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A triphenylene based aromatic compound, having a general formula:

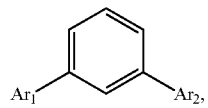

wherein $Ar_1$ is a triphenylenyl group, and $Ar_2$ is a carbazolylphenyl group.

2. The triphenylene based aromatic compound as claimed in claim 1,
wherein $Ar_1$, $Ar_2$, and a benzene center independently have one or more substituents selected from the group consisting of hydrogen, halogen, aryl, halogen-substituted aryl, halogen-substituted aryl alkyl, haloalkyl-substituted aryl, haloalkyl-substituted aryl alkyl, aryl-substituted $C_{1-20}$ alkyl, electron donating group, electron withdrawing group, and heterocyclic-substituents.

3. The triphenylene based aromatic compound as claimed in claim 1, having a general formula:

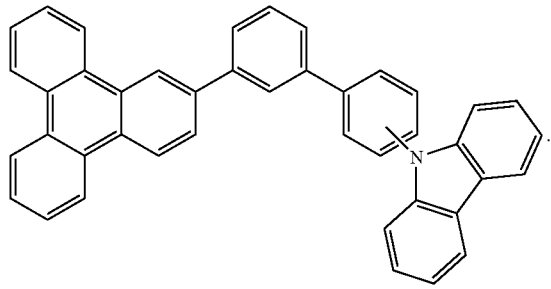

4. An organic light emitting diode, comprising:

an anode;

a cathode; and an organic layer disposed between the anode and the cathode, wherein the organic layer comprises the triphenylene based aromatic compound as claimed in claim 1.

5. The organic light emitting diode as claimed in claim 4, wherein the organic layer comprises a light emitting layer, a hole transporting layer, or combinations thereof.

\* \* \* \* \*